(12) United States Patent
Fukutsuka et al.

(10) Patent No.: US 12,318,241 B2
(45) Date of Patent: Jun. 3, 2025

(54) BIOLOGICAL SOUND MEASUREMENT DEVICE

(71) Applicant: OMRON HEALTHCARE Co., Ltd., Kyoto (JP)

(72) Inventors: Masayuki Fukutsuka, Kyoto (JP); Katsuyoshi Morita, Kyoto (JP); Kosuke Inoue, Kyoto (JP); Seiji Fukunaga, Kyoto (JP); Tsuyoshi Ogihara, Kyoto (JP); Masahiko Yumoto, Kyoto (JP); Yuki Takuma, Kyoto (JP)

(73) Assignee: OMRON HEALTHCARE CO., LTD., Kyoto (JP)

( * ) Notice: Subject to any disclaimer, the term of this patent is extended or adjusted under 35 U.S.C. 154(b) by 714 days.

(21) Appl. No.: 17/305,568

(22) Filed: Jul. 9, 2021

(65) Prior Publication Data

US 2021/0330278 A1 Oct. 28, 2021

Related U.S. Application Data

(63) Continuation of application No. PCT/JP2019/049685, filed on Dec. 18, 2019.

(30) Foreign Application Priority Data

Jan. 11, 2019 (JP) ................. 2019-003488

(51) Int. Cl.
*A61B 7/00* (2006.01)
*A61B 7/04* (2006.01)

(52) U.S. Cl.
CPC ............... *A61B 7/003* (2013.01); *A61B 7/04* (2013.01)

(58) Field of Classification Search
CPC .................................. A61B 7/04; A61B 7/003
See application file for complete search history.

(56) References Cited

U.S. PATENT DOCUMENTS 5,663,532 A 9/1997 Dieken et al.
2018/0067518 A1* 3/2018 Lawrenson ........... G06F 1/1662
(Continued)

FOREIGN PATENT DOCUMENTS

DE 7045017 U 3/1971
DE 696 31 803 T2 1/2005
(Continued)

OTHER PUBLICATIONS

International Preliminary Report on Patentability, dated Aug. 3, 2020, for International Application No. PCT/JP2019/049685.
(Continued)

*Primary Examiner* — Daniel L Cerioni
(74) *Attorney, Agent, or Firm* — Birch, Stewart, Kolasch & Birch, LLP

(57) ABSTRACT

Provided is a biological sound measurement device to improve a measurement accuracy, that includes a sound measurement unit having a contact surface configured to be brought into contact with a body surface, and a gripping portion supporting the sound measurement unit and configured to be gripped by a measurer. The gripping portion is configured to be gripped in a state in which an index finger is placed in a recessed portion, the sound measurement unit includes a sound detector, a housing forming an accommodation space accommodating the sound detector and includes an opening, and a cover closing the opening from outside the accommodation space and forming a pressure-receiving region configured to receive pressure from the body surface. The contact surface is formed by a front surface of the cover, and the opening positioned on a straight (Continued)

line extending in a direction of a force applied from the index finger.

4 Claims, 5 Drawing Sheets

(56) References Cited

U.S. PATENT DOCUMENTS

2018/0177485 A1  6/2018  Yakura et al.
2019/0125270 A1* 5/2019  Deriso ................ A61B 8/488

FOREIGN PATENT DOCUMENTS

| DE | 10 2017 222 589 A1 | 6/2018 |
|---|---|---|
| JP | 117610/1992 | 10/1992 |
| JP | 2000-060845 A | 2/2000 |
| JP | 3139560 U | 2/2008 |
| JP | 2013-123493 A | 6/2013 |
| JP | 3184154 U | 6/2013 |
| JP | 2014-166241 A | 9/2014 |
| JP | 2017-060667 A | 3/2017 |
| JP | 2018-102727 A | 7/2018 |
| JP | 2018-102849 A | 7/2018 |

OTHER PUBLICATIONS

German Office Action for German Application No. 112019005999.8, dated Dec. 19, 2022, with an English translation.

* cited by examiner

[Fig. 1]
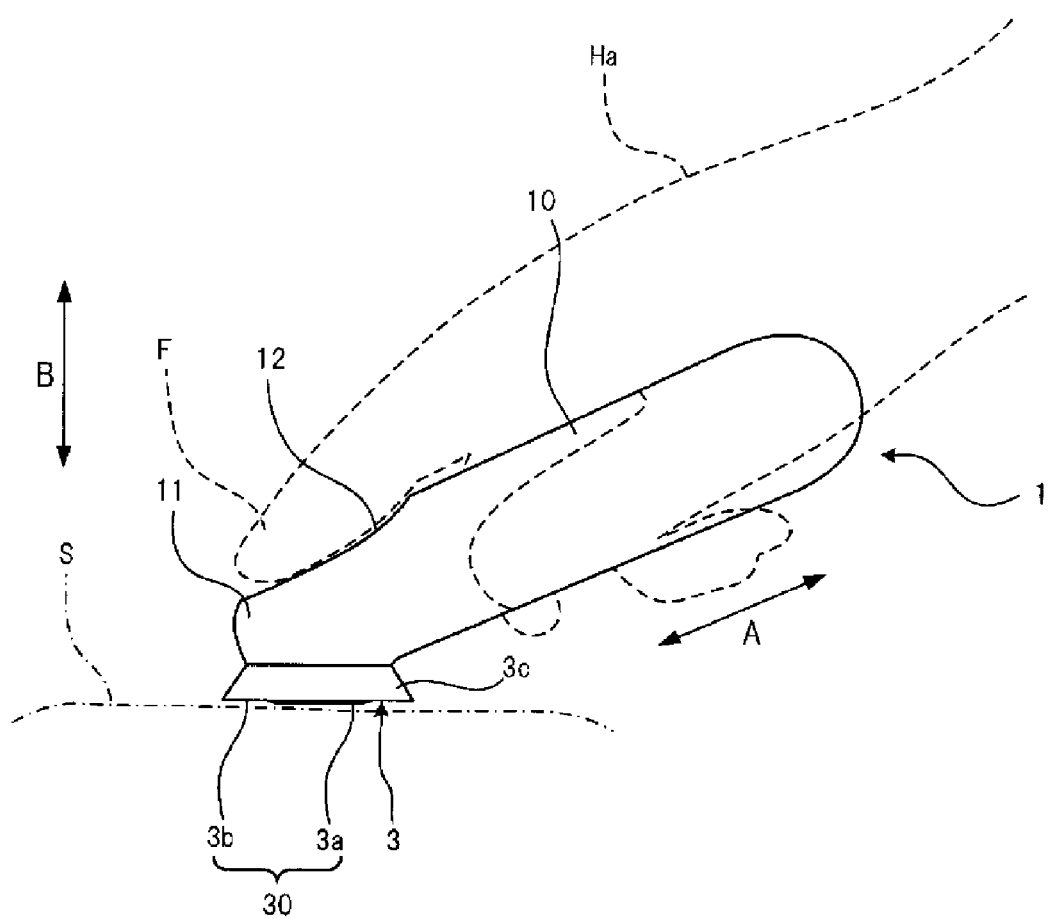

[Fig. 2]
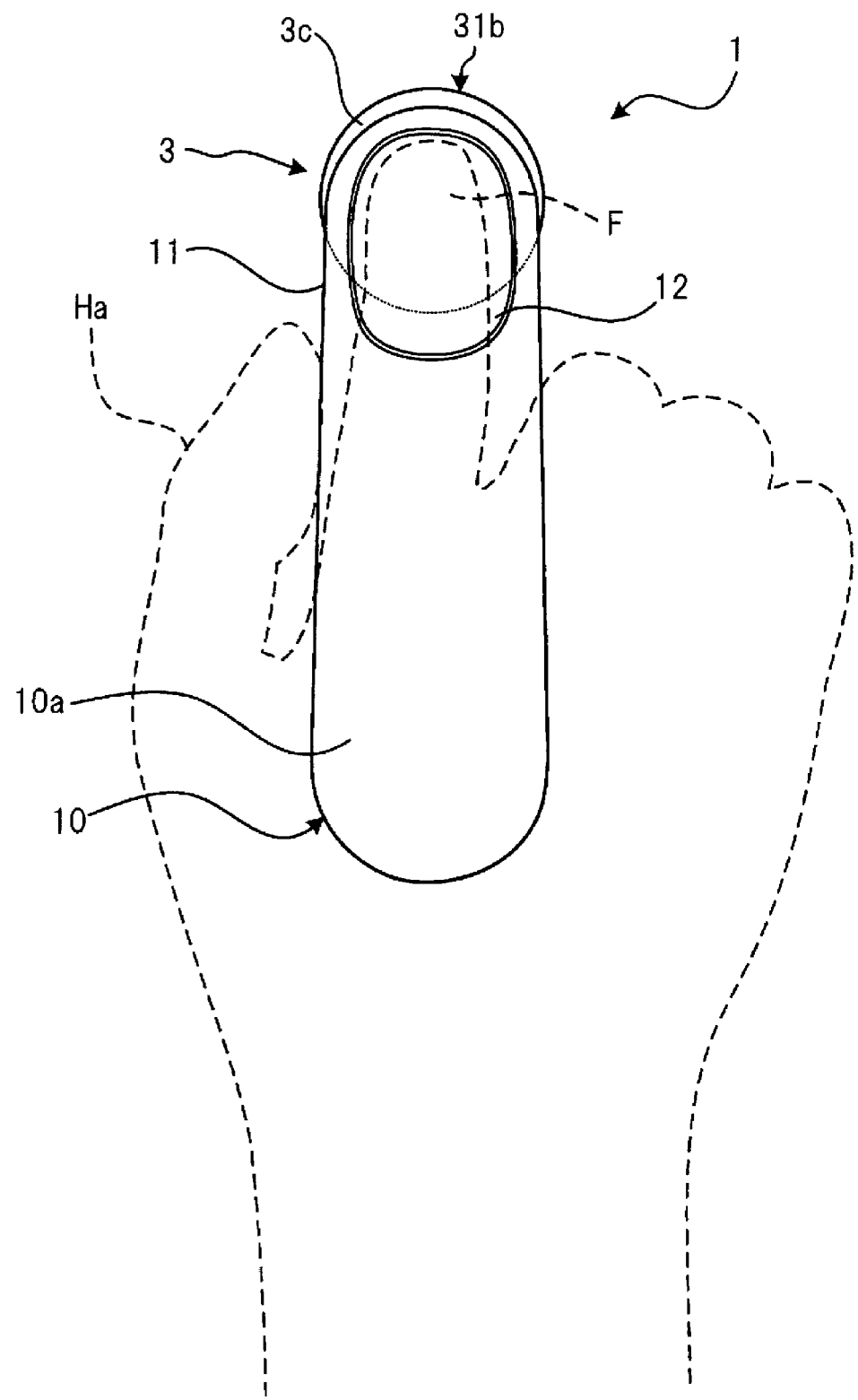

[Fig. 3]
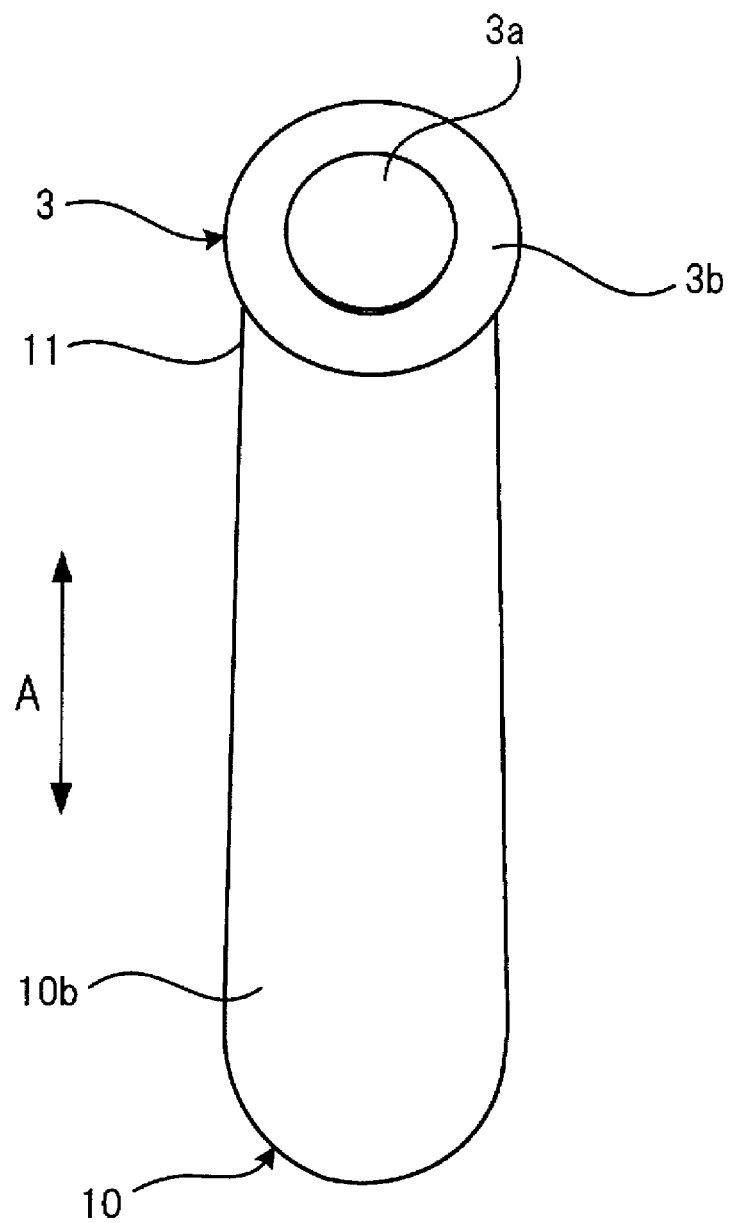

[Fig. 4]
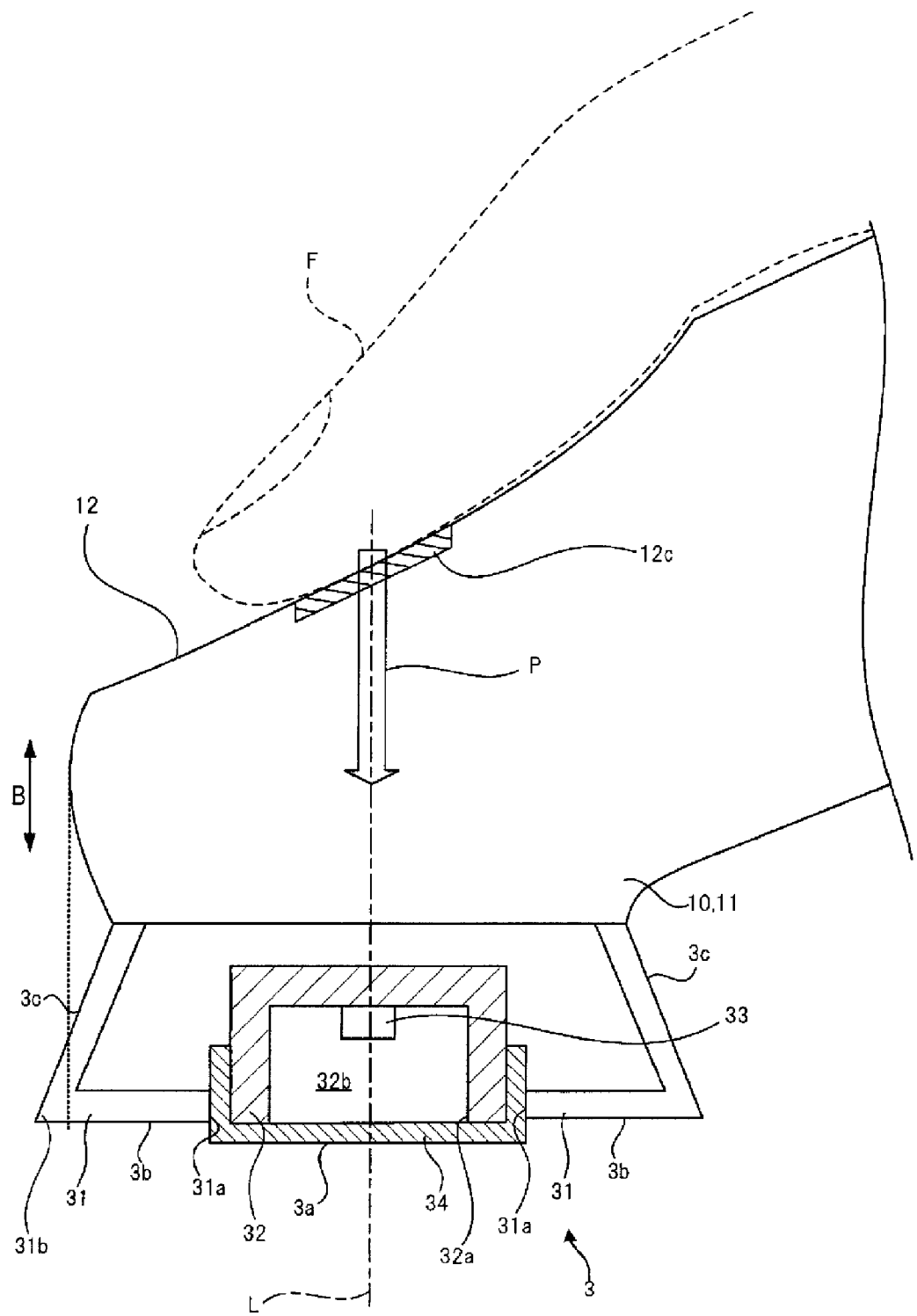

[Fig. 5]
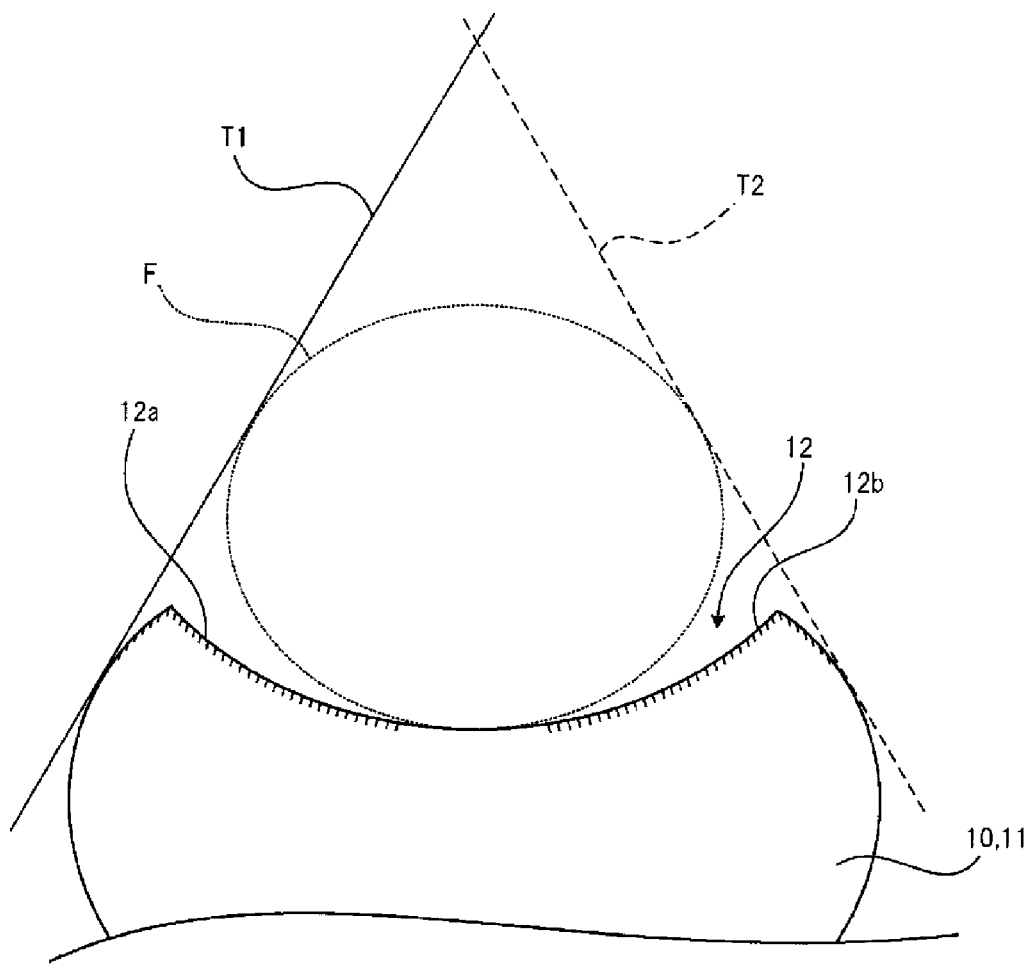

BIOLOGICAL SOUND MEASUREMENT DEVICE

CROSS-REFERENCE TO RELATED APPLICATIONS

This application is the U.S. national stage application filed pursuant to 35 U.S.C. 365(c) and 120 as a continuation of International Patent Application No. PCT/JP2019/049685, filed Dec. 18, 2019, which application claims priority to Japan Patent Application No. 2019-003488, filed Jan. 11, 2019, which applications are incorporated herein by reference in their entireties.

TECHNICAL FIELD

The present invention relates to a biological sound measurement device configured to be brought into contact with the body surface of a subject and measure a biological sound.

BACKGROUND ART

There are known devices configured to utilize a microphone or the like to pick up biological sounds including respiratory sounds, which are physiological sounds that originate from a flow of air generated in the respiratory tract by breathing, adventitious sounds, which are abnormal sounds generated under pathological conditions, such as wheezing or a pleural friction rub, heartbeat sounds that originate from the cardiovascular system, and the like as electrical signals (refer to, for example, Patent Documents 1 to 3).

CITATION LIST

Patent Literature

Patent Document 1: JP 2000-60845 A
Patent Document 2: JP 2013-123493 A
Patent Document 3: JP 2014-166241 A

SUMMARY OF INVENTION

Technical Problem

In order to accurately measure a biological sound, it is necessary to bring the biological sound measurement device into stable contact with the body surface of a living body. Patent Documents 1 to 3 do not recognize these problems.

In light of the foregoing, an object of the present invention is to provide a biological sound measurement device that can facilitate an adjustment of a contact state with the body surface, making it possible to improve a measurement accuracy.

Solution to Problem (1)
A biological sound measurement device configured to measure a biological sound of a subject including a sound measurement unit including a contact surface configured to be brought into contact with the body surface of the subject, and a gripping portion supporting the sound measurement unit and configured to be gripped by a measurer, wherein the gripping portion is configured to be gripped by the measurer in a state in which an index finger of the measurer is placed in a recessed portion formed on a back surface of the sound measurement unit, the sound measurement unit includes a sound detector, a housing that forms an accommodation space accommodating the sound detector and includes an opening, and a cover closing the opening from outside the accommodation space and forming a pressure-receiving region configured to receive pressure from the body surface, the contact surface is formed by a front surface of the cover, and the opening is positioned on a straight line extending in a direction of a force applied to the recessed portion from the index finger in a state in which the contact surface is pressed against the body surface by the index finger placed in the recessed portion.

According to (1), the sound measurement unit can be stably pressed onto the body surface by the index finger, making it possible to increase the measurement accuracy of the biological sound. Further, the pressing force by the index finger is readily transmitted to the opening of the housing, making it easier to increase an adhesion between the pressure-receiving region that closes this opening and the body surface. Thus, the measurement accuracy of the biological sound can be increased.

(2)
The biological sound measurement device according to (1), wherein a plane perpendicular to the straight line and an opening plane of the opening are parallel, and a center of the opening is positioned on the straight line.

According to (2), the pressing force by the index finger is readily transmitted by the opening of the housing, making it easier to increase an adhesion between the pressure-receiving region and the body surface. Thus, the measurement accuracy of the biological sound can be increased.

(3)
The biological sound measurement device according to (1) or (2), wherein the gripping portion is a member extending in one direction, and a longitudinal direction of the gripping portion intersects the contact surface.

According to (3), when the contact surface is brought into contact with the body surface, the gripping portion is disposed at a position away from the body surface. Thus, the possibility of an object such as clothing coming into contact with the gripping portion can be reduced. Accordingly, an occurrence of a rubbing noise between clothing or the like and the gripping portion is suppressed, making it possible to increase the measurement accuracy of the biological sound.

(4)
The biological sound measurement device according to any one of (1) to (3), wherein an inner peripheral surface of the recessed portion is constituted by a member different from a portion of a front surface of the gripping portion surrounding the inner peripheral surface.

According to (4), an interior of the gripping portion can be easily sealed and manufacturing costs can be reduced. Further, a friction coefficient of the inner peripheral surface of the recessed portion, for example, is easier to increase, making it possible to support stable gripping of the gripping portion.

Advantageous Effects of Invention

According to the present invention, it is possible to provide a biological sound measurement device that facilitates adjustment of a contact state with the body surface, making it possible to improve a measurement accuracy.

BRIEF DESCRIPTION OF DRAWINGS

FIG. 1 is a side view schematically illustrating an outline configuration of a biological sound measurement device 1, which is an embodiment of a biological sound measurement device according to the present invention.

FIG. 2 is a schematic view of the biological sound measurement device 1 illustrated in FIG. 1, viewed from a measurer side in a direction B.

FIG. 3 is a schematic view of the biological sound measurement device 1 illustrated in FIG. 2, viewed from a subject side.

FIG. 4 is a cross-sectional schematic view of a sound measurement unit 3 of the biological sound measurement device 1 illustrated in FIG. 1.

FIG. 5 is a schematic view for explaining an object contact avoidance region included in a covered region on a front surface of a gripping portion 10.

DESCRIPTION OF EMBODIMENTS

Overview of Biological Sound Measurement Device of Embodiment

First, an overview of an embodiment of a biological sound measurement device according to the present invention will be described. The biological sound measurement device according to the embodiment is configured to measure, as an example of a biological sound, a pulmonary sound from a subject such as a person (hereinafter also referred to as "person to be measured"), and notify a measurer of an occurrence of wheezing when wheezing is determined to be included in the measured sound. In this way, it is possible to support the determination of the necessity of medication for the person to be measured, the determination of whether or not to take the person to the hospital, and the like.

The biological sound measurement device according to the embodiment includes a sound measurement unit including a contact surface configured to be brought into contact with the body surface of the subject such as a person, and a gripping portion supporting this sound measurement unit and configured to be gripped by a measurer. The gripping portion is gripped in a state in which an index finger is placed in a recessed portion formed on a back surface of the sound measurement unit. Further, the sound measurement unit includes a sound detector, a housing that forms an accommodation space accommodating the sound detector and includes an opening, and a cover closing the opening from outside the accommodation space and forming a pressure-receiving region configured to receive pressure from the body surface. The contact surface is formed by a front surface of the cover. Then, an opening is configured to be positioned on a straight line that extends in a direction of a force applied to the recessed portion from the index finger in a state in which the contact surface is pressed against the body surface by the index finger placed in the recessed portion, thereby facilitating adjustment of the pressing force of the contact surface on the body surface and thus increasing the measurement accuracy.

A specific configuration example of the biological sound measurement device according to the embodiment will be described below.

Embodiment

FIG. 1 is a side view schematically illustrating an outline configuration of a biological sound measurement device 1, which is an embodiment of the biological sound measurement device according to the present invention. FIG. 2 is a schematic view of the biological sound measurement device 1 illustrated in FIG. 1, viewed from the measurer side in a direction B. FIG. 3 is a schematic view of the biological sound measurement device 1 illustrated in FIG. 2, viewed from the subject side. FIG. 4 is a cross-sectional schematic view of a sound measurement unit 3 of the biological sound measurement device 1 illustrated in FIG. 1.

As illustrated in FIG. 1 to FIG. 3, the biological sound measurement device 1 includes a gripping portion 10 having a columnar shape extending in a longitudinal direction A and constituted by a case of a resin, a metal, or the like. A head portion 11 is provided on one end side of this gripping portion 10. The gripping portion 10 is a portion gripped by one hand Ha of the measurer. A size of the gripping portion 10 is configured in a size to the extent that a length in the longitudinal direction A can be substantially accommodated inside the hand Ha, and a width and a thickness can be gripped and held by one hand of an adult.

An integrated control unit (not illustrated) configured to integrally control the entire biological sound measurement device 1, a battery (not illustrated) configured to supply a voltage required for operation, and the like are provided inside the gripping portion 10.

The integrated control unit includes various processors, random access memory (RAM), read only memory (ROM), and the like, and performs a control and the like of each hardware of the biological sound measurement device 1 in accordance with a program. For example, the integrated control unit performs a process of analyzing the pulmonary sound detected by a sound detector 33 described later, and notifying of an analysis result such as the presence or absence of wheezing.

As illustrated in FIG. 1 and FIG. 4, the head portion 11 is provided with the sound measurement unit 3 that protrudes toward one side (lower side in FIG. 1 and FIG. 4) in a direction intersecting the longitudinal direction A of the gripping portion 10. A contact surface 30 configured to be brought into contact with the body surface S of the subject is provided on a tip end of this sound measurement unit 3.

The contact surface 30 is constituted by a pressure-receiving region 3a (refer to FIG. 3) having a circular shape, for example, and an extended region 3b (refer to FIG. 3) having an annular shape, for example. The pressure-receiving region 3a is a flat surface required for receiving pressure from the body surface S, and the extended region 3b is a flat surface formed around the pressure-receiving region 3a and provided to increase a contact area with the body surface S. In the example of FIG. 1 and FIG. 4, the pressure-receiving region 3a protrudes slightly further toward the body surface S side than the extended region 3b, but may be formed on the same plane as the extended region 3b. The direction B illustrated in FIG. 1 is a direction perpendicular to the contact surface 30 and intersects the longitudinal direction A of the gripping portion 10.

As illustrated in FIG. 2 and FIG. 4, in a state of viewing in the direction B perpendicular to the contact surface 30, a recessed portion 12 for placement of an index finger F of the hand Ha of the measurer is formed on a surface 10a of the gripping portion 10, which is opposite side to the sound measurement unit 3 side, on a portion overlapping the sound measurement unit 3 (back surface of the sound measurement unit 3).

As illustrated in FIG. 1 and FIG. 2, the biological sound measurement device 1 is used, in a state in which the index finger F of the hand Ha of the measurer is placed in the recessed portion 12 of the gripping portion 10 and the gripping portion 10 is gripped by the hand Ha, with the contact surface 30 including the pressure-receiving region 3a of the sound measurement unit 3 being pressed against the body surface S by the index finger F.

As illustrated in FIG. 4, the sound measurement unit 3 includes the sound detector 33 such as a micro-electromechanical systems (MEMS) type microphone or a capacitive microphone, and a housing 32 having a bottomed tubular shape, forming an accommodation space 32b accommodating the sound detector 33, and including an opening 32a, a cover 34 closing the opening 32a from outside the accommodation space 32b and forming the pressure-receiving region 3a that receives pressure from the body surface S, and a case 31 supported by the gripping portion 10 and accommodating the housing 32 and the cover 34 in a state in which the cover 34 is exposed.

The housing 32 is made of a material having higher acoustic impedance than that of air and high rigidity, such as resin or metal. The housing 32 is preferably made of a material that reflects sound in a detection frequency band of the sound detector 33 in a sealed state of the housing 32 so that sound is not transmitted from the outside to the interior of the accommodation space 32b.

The cover 34 is a member having a bottomed tubular shape, and a shape of a hollow portion thereof substantially matches an outer wall shape of the housing 32. The cover 34 is made of a material having a flexibility, an acoustic impedance close to that of the human body, air, or water, and favorable biocompatibility. Examples of the material of the cover 34 include silicone and an elastomer.

The case 31 is made of resin, for example. The case 31 is formed with an opening 31a at an end portion of opposite side to the gripping portion 10 side, and a portion of the cover 34 is in a protruding and exposed state from this opening 31a. A front surface of the cover 34 exposed from this case 31 forms the pressure-receiving region 3a described above.

When the pressure-receiving region 3a is brought into close contact state with the body surface S, vibration of the body surface S generated by the pulmonary sound of the living body vibrates the cover 34. When the cover 34 vibrates, an internal pressure of the accommodation space 32b fluctuates due to this vibration and, by this internal pressure fluctuation, an electrical signal corresponding to the pulmonary sound is detected by the sound detector 33.

As illustrated in FIG. 4, the biological sound measurement device 1 is configured so that, in a state in which the contact surface 30 is pressed against the body surface S by the index finger F of the measurer placed in the recessed portion 12 of the gripping portion 10, a direction of a force P (indicated by the white arrow in FIG. 4) applied to the recessed portion 12 from the index finger F is perpendicular to the contact surface 30 (in other words, perpendicular to an opening plane of the opening 32a).

Further, in the biological sound measurement device 1, a region 12c where the force P is applied, in a state in which the index finger F of the hand Ha having various possible sizes is placed in the recessed portion 12, is established in the recessed portion 12. The region 12c is experimentally determined. This region 12c and the opening 32a overlap when viewed in the direction B. That is, the opening 32a is configured to be positioned on a straight line extending in the direction of the force P applied to the region 12c.

FIG. 4 illustrates a straight line L extending in the direction of the force P applied to a center of the region 12c. A plane perpendicular to this straight line L and the opening plane of the opening 32a are parallel. Further, in a state of viewing from the direction B, this straight line L and a center of the opening 32a overlap.

As illustrated in FIG. 4, an outer surface of the portion of the case 31 protruding from the gripping portion 10 is constituted by the extended region 3b described above, which is formed of a flat surface having an annular shape, and a tapered surface 3c that connects an outer peripheral edge of the extended region 3b and the gripping portion 10. The tapered surface 3c is a surface having an outer diameter that continuously increases from the gripping portion 10 side toward the extended region 3b side.

As illustrated in FIG. 2, the sound measurement unit 3 and the gripping portion 10 partially overlap. In FIG. 2, a non-overlapping portion 31b of the sound measurement unit 3 positioned outside the gripping portion 10 includes the contact surface 30 described above. Then, a width of the non-overlapping portion 31b in a direction parallel to the contact surface 30 is greatest at a first position, which is a position of the contact surface 30 in the direction B (defined as the position of the extended region 3b). Further, at a position closer to the gripping portion 10 than the first position in the direction B, the width of the non-overlapping portion 31b in the direction parallel to the contact surface 30 is less than the width at the first position.

In other words, a cross-sectional area of a cross section of the non-overlapping portion 31b parallel to the contact surface 30 (area of the region surrounded by an outer edge of the non-overlapping portion 31b) is greatest at the first position and, at a position closer to the gripping portion 10 than the first position, is less than the cross-sectional area at the first position.

Of the front surface of the gripping portion 10 of the biological sound measurement device 1, at least a region (hereinafter referred to as "first region") excluding the region to be covered by the hand Ha of the measurer in a state in which the gripping portion 10 is gripped by the hand Ha of the measurer (hereinafter referred to as "covered region") is a region not including an angular portion. A surface not including an angular portion refers to a surface that is smooth to the extent that an object such as clothing is unlikely to get caught and friction with an object such as clothing is unlikely to occur.

Note that, as the gripping portion 10, a single member integrally molded without a seam or a member formed by joining a plurality of components without unevenness can be adopted. Further, regardless of whether the gripping portion 10 is constituted by one member or a plurality of members, a configuration in which an operation button, for example, is embedded in a surface portion of the gripping portion 10 without unevenness is also possible. When the gripping portion 10 has a configuration in which a plurality of components are joined together, or when an operation button or the like is embedded in the gripping portion 10, or the like, a configuration in which a joining portion (boundary portion) of the plurality of components and a boundary portion between the gripping portion 10 and the operation button or the like exist in the first region described above on the front surface of the gripping portion 10 is conceivable. However, it is unlikely that an object, such as clothing, will get caught on such a boundary portion of two members that is substantially free of unevenness. Therefore, when this boundary portion exists in the first region, as long the portion of the first region excluding this boundary portion is free of an angular portion, the first region can be regarded as having a configuration of not including an angular portion.

The covered region described above is constituted by a region (hereinafter referred to as a hand contact region) that can be brought into contact with the hand Ha of various possible sizes with the gripping portion 10 gripped by the hand Ha of each size, and a region (hereinafter referred to as an object contact avoidance region) around the index finger F that, in a state in which the index finger F of the hand Ha of each size is placed in the recessed portion 12, is assumed to be hindered from contact with an object by the index finger F. This object contact avoidance region and the region in contact with the index finger F on the front surface of the gripping portion 10 constitute a region to be covered by the index finger F.

FIG. 5 is a schematic view for explaining the object contact avoidance region included in the covered region on the front surface of the gripping portion 10. FIG. 5 is a cross-sectional schematic view of a portion of the gripping portion 10 where the recessed portion 12 is formed, taken along a plane perpendicular to the longitudinal direction A at any position in the longitudinal direction A.

As illustrated in FIG. 5, the gripping portion 10 and the recessed portion 12 of the biological sound measurement device 1 are designed so that, in a state in which the index finger F is placed in the recessed portion 12, it is possible to draw a tangent line T1 common to a front surface of the index finger F and a region of the front surface of the gripping portion 10 on one side (left side in FIG. 5) of the gripping portion 10 in the lateral direction from the recessed portion 12, and to draw a tangent line T2 common to the front surface of the index finger F and a region of the front surface of the gripping portion 10 on the other side (right side in FIG. 5) in the lateral direction of the gripping portion 10 from the recessed portion 12.

With such a design, a range 12a (shaded region in FIG. 5) of the front surface of the gripping portion 10 surrounded by the tangent line T1 and the index finger F in the cross-sectional view illustrated in FIG. 5 is a range in which contact with an object is presumably hindered by the index finger F. Similarly, a range 12b (shaded region in FIG. 5) of the front surface of the gripping portion 10 surrounded by the tangent line T2 and the index finger F in the cross-sectional view illustrated in FIG. 5 is a range in which contact with an object is presumably hindered by the index finger F. That is, in the biological sound measurement device 1, the ranges 12a and 12b illustrated in FIG. 5 are object contact avoidance regions.

Note that, in consideration of ease of manufacture and a designability of the device, the front surface of the gripping portion 10 is preferably configured so that all regions excluding the recessed portion 12 and edge portions thereof are not including an angular portion. A bottom surface of the recessed portion 12 is preferably a surface that has a large friction coefficient in order to stabilize a gripping posture of the gripping portion 10, but of course an inner surface of the recessed portion 12 may be configured without an angular portion.

Effects of Biological Sound Measurement Device 1

As described above, according to the biological sound measurement device 1, at least the first region of the front surface of the gripping portion 10, excluding the covered region (hand contact region and object contact avoidance region) is a region not including an angular portion. Therefore, even when clothing or the like comes into contact with the first region where contact with clothing or the like is possible, the clothing is prevented from getting caught on the first region and the friction between the clothing and the first region is prevented from increasing, thereby making it possible to suppress the occurrence of a rubbing noise. With the occurrence of a rubbing noise suppressed, it is possible to suppress noise transmitted to the sound detector 33. Thus, the measurement accuracy of the biological sound can be improved.

Further, in the biological sound measurement device 1, the recessed portion 12 for placement of the index finger F is formed in a region (object contact avoidance region and contact region with the index finger F) to be covered by the index finger F of the measurer in a state in which the gripping portion 10 is gripped by the measurer. According to this configuration, the sound measurement unit 3 can be stably pressed onto the body surface S by the index finger F, making it possible to increase the measurement accuracy of the biological sound. Further, with placement of the index finger F, a wide range of the gripping portion 10 is covered by the hand. Thus, a range of the front surface of the gripping portion 10 with which clothing or the like can come into contact can be reduced, making it possible to effectively suppress the occurrence of a rubbing noise.

With formation of the recessed portion 12 on the back surface of the sound measurement unit 3, a distance between the contact surface 30 and the index finger F can be shortened, making the pressing of the contact surface 30 easily felt by the index finger F and the pressing force easily to be adjusted and easily to be applied to the intended position. Note that, in the gripping portion 10, the inner peripheral surface of the recessed portion 12 may be a component separate from the portion surrounding this inner peripheral surface, for example. With such a configuration, water resistance can be ensured by the recessed portion 12 even in a configuration in which a threaded hole for assembly of a structural component in the interior of the gripping portion 10 or a sound-emitting hole for notifications is provided in a portion where the inner peripheral surface of the recessed portion 12 is attached. Further, this also facilitates use of a material having a high friction coefficient (specifically, a material having a higher friction coefficient than that of the first region) as the inner peripheral surface of the recessed portion 12, making a shift in position of the index finger F less likely and stable pressing possible when the force P is applied to the inner peripheral surface of the recessed portion 12.

Further, in the biological sound measurement device 1, the opening 32a of the housing 32 of the sound measurement unit 3 is positioned on a straight line extending from the index finger F in the direction of the force P applied to the recessed portion 12 in a state in which the contact surface 30 is pressed against the body surface S by the index finger F placed in the recessed portion 12. According to this configuration, the pressing force by the index finger F is readily transmitted to the opening 32a of the housing 32, making it easier to increase an adhesion between the pressure-receiving region 3a that closes this opening 32a and the body surface S. Thus, the measurement accuracy of the biological sound can be increased.

Further, in the biological sound measurement device 1, a plane perpendicular to the straight line L described above and an opening plane of the opening 32a are parallel, and the center of the opening 32a is positioned on the straight line L. According to this configuration, the pressing force by the index finger F is readily transmitted to the opening 32a of the housing 32, making it easier to increase the adhesion between the pressure-receiving region 3a and the body surface S. As a result, the measurement accuracy of the biological sound can be further increased.

Further, in the biological sound measurement device 1, the contact surface 30 and the longitudinal direction A of the gripping portion 10 intersect. More specifically, in a state in which the longitudinal direction A of the gripping portion 10 is substantially parallel to the body surface of the subject, the contact surface 30 is configured to be inclined from the body surface S side toward the gripping portion 10 side. According to this configuration, in a state in which the contact surface 30 is in contact with the body surface S, the gripping portion 10 is disposed at a position away from the body surface S. Therefore, the possibility of an object such as clothing coming into contact with the first region described above of the gripping portion 10 can be reduced. Accordingly, the occurrence of a rubbing noise can be more effectively suppressed.

Further, according to the biological sound measurement device 1, in a state in which the contact surface 30 of the sound measurement unit 3 is in contact with the body surface S, the outer edge of the non-overlapping portion 31b not overlapping the gripping portion 10 of the sound measurement unit 3 becomes the outer edge of the contact surface 30 as is, and is visible. Therefore, the contact state between the contact surface 30 and the body surface S can be easily confirmed. As a result, a favorable contact state can be easily achieved, making it possible to improve the measurement accuracy of the biological sound.

Further, according to the biological sound measurement device 1, the side surface of the sound measurement unit 3 excluding the contact surface 30 of the case 31 is the tapered surface 3c that decreases in diameter (width) from the contact surface 30 toward the gripping portion 10. This makes it possible to secure space for avoiding interference with clothing, a bone, and the like between the tapered surface 3c and the gripping portion 10 while increasing the area of the contact surface 30 to enable stable contact with the body surface S. As a result, preparatory work prior to the start of measurement of the biological sound can be performed smoothly. In particular, in a device configured to detect wheezing from a pulmonary sound, the subject is presumably an infant or the like. An infant presumably moves frequently and thus, with this work being performed smoothly, the burden on the measurer can be alleviated.

Further, according to the biological sound measurement device 1, the longitudinal direction A of the gripping portion 10 and the contact surface 30 intersect. Thus, in a state in which the contact surface 30 is in contact with the body surface S, the gripping portion 10 is not parallel to the body surface S. In such a configuration, the outer edge of the non-overlapping portion 31b becomes visible as an outer edge of the contact surface 30 as is and, regardless of the orientation of the gripping portion 10, the contact state between the contact surface 30 and the body surface S can be intuitively determined. As a result, it is possible to improve the measurement accuracy of the biological sound while alleviating the burden on the measurer.

Modified Example of Biological Sound Measurement Device 1

Preferably, an outer surface of the case 31 of the sound measurement unit 3 is also configured without an angular portion. According to this configuration, it is possible to prevent an object such as clothing from getting caught on the front surface of the sound measurement unit 3 and an increase in friction, and thus suppress the occurrence of a rubbing noise.

The recessed portion 12 in the gripping portion 10 is not required and may be omitted. In this case, the contact surface 30 is pressed against the body surface S while the gripping portion 10 is gripped in a state in which the measurer is placing the index finger F on the position where the recessed portion 12 should be formed to achieve a state appropriate for measurement of the biological sound.

When the recessed portion 12 is thus omitted, a region of the front surface of the gripping portion 10 other than the hand contact region is at least configured without an angular portion, making it possible to prevent an object such as clothing from getting caught on the front surface of the gripping portion 10 and an increase in friction in a state in which the gripping portion 10 is gripped, and thus suppress the occurrence of a rubbing noise. In a configuration in which the recessed portion 12 is omitted, the hand contact region of the front surface of the gripping portion 10 constitutes the covered region (region to be covered by the hand) described above.

Note that, in a configuration in which the recessed portion 12 is omitted, the entire front surface of the gripping portion 10 may be configured without an angular portion. With such a configuration, it is possible to more effectively prevent an object such as clothing from getting caught on the front surface of the gripping portion 10 and the like, and thus suppress the occurrence of a rubbing noise. Further, the designability of the device can also be improved.

In the biological sound measurement device 1, the longitudinal direction A of the gripping portion 10 and the contact surface 30 may be configured to be parallel. Further, the side surface of the case 31 may be a surface parallel to the direction B, for example, rather than the tapered surface 3c. Further, the sound measurement unit 3 may be configured to be completely concealed by the gripping portion 10 (configured without the non-overlapping portion 31b) in a state of viewing from the direction B. Further, the extended region 3b of the contact surface 30 is not required and may be omitted. Further, the first region of the front surface of the gripping portion 10 may be configured to include an angular portion.

While various embodiments have been described with reference to the drawings, needless to say, the present invention is not limited to such examples. It will be apparent to those skilled in the art that various changes and modifications can be made within the scope of the claims, and it is understood that these are naturally belong within the technical scope of the present invention. Further, each of the components of the above-described embodiments may be combined as desired within a range that does not depart from the spirit of the present invention.

Note that the present application is based on Japanese Patent Application filed Jan. 11, 2019 (JP 2019-003488), the contents of which are incorporated herein by reference.

REFERENCE SIGNS LIST

1 Biological sound measurement device
3 Sound measurement unit
10 Gripping portion
10a, 10b Surface
11 Head portion
12 Recessed portion
12a, 12b Range
12c Region
3a Pressure-receiving region
3b Extended region
3c Tapered surface
30 Contact surface
31 Case
31a, 32a Opening
31b Non-overlapping portion
32 Housing
32b Accommodation space
33 Sound detector
34 Cover
S Body surface Ha Hand
F Index finger
T1, T2 Tangent line
L Straight line
P Force

The invention claimed is:

1. A biological sound measurement device configured to measure a biological sound of a subject comprising:
   a gripping portion having a columnar shape extending in a longitudinal direction from a proximal end portion to a distal end portion and configured to be gripped by a measurer measuring the biological sound; and
   a sound measurement unit including a contact surface configured to be brought into contact with the body surface of the subject, the sound measurement unit being disposed at the distal portion of the gripping portion so that the contact surface is inclined to the longitudinal direction of the distal portion of the gripping portion, wherein a recessed portion for placement of an index finger is formed on an upper surface of the gripping portion opposite to a lower surface supporting the sound measurement unit, at a position corresponding to a back surface of the sound measurement unit, and the gripping portion is configured to be gripped by the measurer in a state in which an index finger of the measurer is placed in the recessed portion,
   the sound measurement unit includes a sound detector, a housing that forms an accommodation space accommodating the sound detector and including an opening, and a cover closing the opening from outside the accommodation space and forming a pressure-receiving region configured to receive pressure from the body surface,
   the contact surface is formed by a front surface of the cover,
   the opening is positioned on a straight line extending in a direction of a force applied to the recessed portion from the index finger when in a state in which the contact surface is pressed against the body surface by the index finger placed in the recessed portion, and
   the upper surface of the distal portion of the gripping portion that has the recessed portion and the longitudinal direction of the distal portion of the gripping portion are inclined to the contact surface of the sound measurement unit in the state in which the contact surface is pressed against the body surface by the index finger placed in the recessed portion.

2. The biological sound measurement device according to claim 1, wherein
   a plane perpendicular to the straight line and an opening plane of the opening are parallel, and
   a center of the opening is positioned on the straight line.

3. The biological sound measurement device according to claim 1, wherein an inner peripheral surface of the recessed portion is constituted by a member different from a portion of a front surface of the gripping portion surrounding the inner peripheral surface.

4. The biological sound measurement device according to claim 1, wherein an inner peripheral surface of the recessed portion is constituted by a member different from a portion of a front surface of the gripping portion surrounding the inner peripheral surface, so that a friction coefficient of the inner peripheral surface of the recessed portion is higher than that of the portion of the front surface of the gripping portion surrounding the inner peripheral surface.

* * * * *